United States Patent
Skulachev et al.

(10) Patent No.: US 10,188,669 B2
(45) Date of Patent: Jan. 29, 2019

(54) MITOCHONDRIA-TARGETED ANTIOXIDANTS FOR TREATMENT OF AGE-RELATED BRAIN DISORDERS

(71) Applicant: MITOTECH S.A., Luxembourg (LU)

(72) Inventors: Maxim Vladimirovich Skulachev, Moscow (RU); Vladimir Petrovich Skulachev, Moscow (RU); Maxim Viktorovich Egorov, Moscow (RU); Nikolai Konstantinovich Isaev, Moscow Region (RU); Nadezhda Anatolievna Kapay, Moscow Region (RU); Dmitry Borisovich Zorov, Moscow (RU); Elena Viktorovna Stelmashuk, Moscow Region (RU); Fedor Fedorovich Severin, Moscow (RU)

(73) Assignee: MITOTECH S.A., Luxembourg (LU)

(*) Notice: Subject to any disclaimer, the term of this patent is extended or adjusted under 35 U.S.C. 154(b) by 0 days.

(21) Appl. No.: 15/058,903

(22) Filed: Mar. 2, 2016

(65) Prior Publication Data

US 2016/0354392 A1 Dec. 8, 2016

Related U.S. Application Data

(62) Division of application No. 14/353,645, filed as application No. PCT/US2012/056613 on Sep. 21, 2012, now abandoned.

(60) Provisional application No. 61/537,701, filed on Sep. 22, 2011.

(51) Int. Cl.
| | |
|---|---|
| *A61K 31/66* | (2006.01) |
| *A61K 31/35* | (2006.01) |
| *A61K 45/06* | (2006.01) |
| *A61K 31/352* | (2006.01) |
| *A61K 31/444* | (2006.01) |
| *A61K 47/54* | (2017.01) |

(52) U.S. Cl.
CPC ............ *A61K 31/66* (2013.01); *A61K 31/352* (2013.01); *A61K 31/444* (2013.01); *A61K 45/06* (2013.01); *A61K 47/54* (2017.08); *A61K 47/545* (2017.08)

(58) Field of Classification Search
None
See application file for complete search history.

(56) References Cited

U.S. PATENT DOCUMENTS

| | | | | |
|---|---|---|---|---|
| 6,331,532 | B1* | 12/2001 | Murphy | A61K 31/66 514/100 |
| 2010/0234326 | A1* | 9/2010 | Skulachev | A61K 31/66 514/125 |
| 2011/0053895 | A1 | 3/2011 | Skulachev et al. | |

FOREIGN PATENT DOCUMENTS

WO 2007/046729 A1 4/2007

OTHER PUBLICATIONS

Manzo et al. Int. J. Environ. Res. Public Health 2010, 7, 4281-4304.*
Tyagi et al. Journal of Cellular Biochemistry 96:665-671 (2005).*
Ingram et al. Experimental Gerontology 46 (2011) 148-154.*
Azizi, Z. A., et al., "Effects of hyperhomocysteinemia during the gestational period on ossification in rat embryo", Bone 46 (2010), pp. 1344-1348.
Bhate, V., et al., "Vitamin B12 status of pregnant Indian women and cognitive function in their 9-year-old children", Food Nutr bull. Dec. 2008, 29(4), pp. 249-254.
Bravo, E., et al., "High fat diet-induced non alcoholic fatty liver disease in rats is associated with hyperhomocysteinemia caused by down regulation of the transsulphuration pathway", Lipids in Health an Disease 2011, 10:60, pp. 1-6.
Deshmukh, U. S., et al., "Effect of physiological doses of oral vitamin B12 on plasma homocysteine—A randomized, placebo-controlled, double-blind trial in India", Eur J Clin Nutr. May 2010, 64(5), pp. 495-502.
Goldstein, N., "Reactive Oxygen Species as Essential Components of Ambient Air", Biochemistry (Moscow), vol. 67, No. 2, 2002, pp. 161-170.
Gorgone, G., et al., "Hyperhomocysteinemia in patients with epilepsy: Does it play a role in the pathogenesis of brain atrophy? A preliminary report", Epilepsia, 50(Suppl. 1), 2009, pp. 33-36.
Haass, C., et al., "Soluble protein oligomers in neurodegeneration: lessons from the Alzheimer's amyloid β-peptide", Nature Reviews Molecular Cell Biology, vol. 8, Feb. 2007, pp. 101-112.
Herrmann, W., et al., "Homocysteine: a biomarker in neurodegenerative diseases", Clin Chem Lab Med 2011 49(3), pp. 435-441.
Honzik, T., et al., "Clinical presentation and metabolic consequences in 40 breastfed infants with nutritional vitamin B12 deficiency—What have we learned?", European Journal of Paediatric Neurology 14 (2010), pp. 488-495.
Jolkkonen, J., et al., "Behavioral effects of the $\alpha_2$-adrenoceptor antagonist, atipamezole, after focal cerebral ischemia in rats", European Journal of Pharmacology 400 (2000), pp. 211-219.
Karl, T., et al., "Behavioral phenotyping of mice in pharmacological and toxicological research", Exp Toxic Pathol 2003, 55, pp. 69-83.
Karalezli, A., et al., "Homocysteine and Serum-Lipid Levels in Pulmonary Embolism", Clinical and Applied Thrombosis/Hemostasis 17(6), pp. E186-E189.

(Continued)

*Primary Examiner* — Jeffrey S Lundgren
*Assistant Examiner* — Michael J Schmitt
(74) *Attorney, Agent, or Firm* — Ladas & Parry LLP

(57) ABSTRACT

A method for providing to a mammal a neuroprotective effect against a brain pathology that is associated with reactive oxygen species originating from mitochondria (mROS). The method includes the step of administering to the mammal an SkQ mitochondria-targeted antioxidant in an amount effective to provide said neuroprotective effect. The SkQ mitochondria-targeted antioxidant may be administered either prophylactically or for treatment with respect to brain pathologies other than brain trauma or stroke, and may be administered for treatment of brain trauma or stroke.

15 Claims, 17 Drawing Sheets

(56) References Cited

OTHER PUBLICATIONS

Kolling, J., et al., "Homocysteine Induces Oxidative—Nitrative Stress in Heart of Rats: Prevention by Folic Acid", Cardiovasc Toxicol (2011), 11, pp. 67-73.
Lloret, A., et al., "Alzheimer's amyloid-β toxicity and tau hyperphosphorylation are linked via RCAN1", J Alzheimers Dis. 2011, 27(4), pp. 701-709.
Lott, I. T., et al., "Down Syndrome and Dementia: A Randomized, Controlled Trial of Antioxidant Supplementation", Am J Med Genet A. Aug. 2011, 155A(8), pp. 1939-1948.
Maire, F., et al., "Factors associated with hyperhomocysteinemia in Crohn's disease", Gastroenterol Clin Biol 2001, 25, pp. 745-748.
Makhro, A.V., et al., "Prenatal Hyperhomocysteinemia as a Model of Oxidative Stress of the Brain", Bulletin of Experimental Biology and Medicine, vol. 146, No. 1, 2008, pp. 33-35.
Malenka, R. C., et al., "Long-Term Potentiation—A Decade of Progress?", Science, vol. 285, Sep. 17, 1999, pp. 1870-1874.
Molloy, A.M., et al., "Maternal Vitamin $B_{12}$ Status and Risk of Neural Tube Defects in a Population With High Neural Tube Defect Prevalence and No Folic Acid Fortification", Pediatrics, 2009, Mar. 123(3), pp. 917-923.
Murphy, M.M., et al., "Homocysteine in Pregnancy", Advances in Clinical Chemistry, vol. 53, pp. 105-137.
Murphy, M.P., et al., "Targeting Antioxidants to Mitochondria by Conjugation to Lipophilic Cations", Annu. Rev. Pharmacol. Toxicol. 2007, 47, pp. 629-656.
Oddo, S., et al., "Triple-Transgenic Model of Alzheimer's Disease with Plaques and Tangles: Intracellular Aβ and Synaptic Dysfunction", Neuron, vol. 39, Jul. 31, 2003, pp. 409-421.
Pagani, L., et al., "Amyloid-Beta Interaction with Mitochondria", International Journal of Alzheimer's Disease, vol. 2011, pp. 1-12.
Petit-Demouliere, B., et al., "Forced swimming test in mice: a review of antidepressant activity", Psychopharmacology (2005), 177, pp. 245-255.
Plotnikov, E.Y., et al., "New-Generation Skulachev Ions Exhibiting Nephroprotective and Neuroprotective Properties", Biochemistry (Moscow), 2010, vol. 75, No. 2, pp. 145-150.
Rogers, E. J., "Has enhanced folate status during pregnancy altered natural selection and possibly Autism prevalence? A closer look at a possible link", Medical Hypotheses (2008), 71, pp. 406-410.
Selkoe, D. J., "Alzheimer's Disease Is a Synaptic Failure", Science, vol. 298, Oct. 25, 2002, pp. 789-791.
Snow, B. J., et al., "A Double-Blind, Placebo-Controlled Study to Assess the Mitochondria-Targeted Antioxidant MitoQ as a Disease-Modifying Therapy in Parkinson's Disease", Movement Disorders, vol. 25, No. 11, 2010, pp. 1670-1674.
Stefanova, N.A., et al., "Behavioral Effects Induced by Mitochondria-Targeted Antioxidant SkQ1 in Wistar and Senescence-Accelerated OXYS Rats", Journal of Alzheimer's Disease, 21 (2010), pp. 479-491.
Treit, D., et al., "Anxiogenic Stimuli in the Elevated Plus-Maze", Pharmacology Biochemistry and Behavior, vol. 44, pp. 463-469.
Vollset, S. E., et al., Plasma total homocysteine, pregnancy complications, and adverse pregnancy outcomes: the Hordaland Homocysteine Study[1-3], Am J Clin Nutr 2000, 71, pp. 962-968.
Xu, Y., et al., "Methionine diet-induced hyperhomocysteinemia accelerates cerebral aneurysm formation in rats", Neuroscience Letters 494 (2011), pp. 139-144.

* cited by examiner

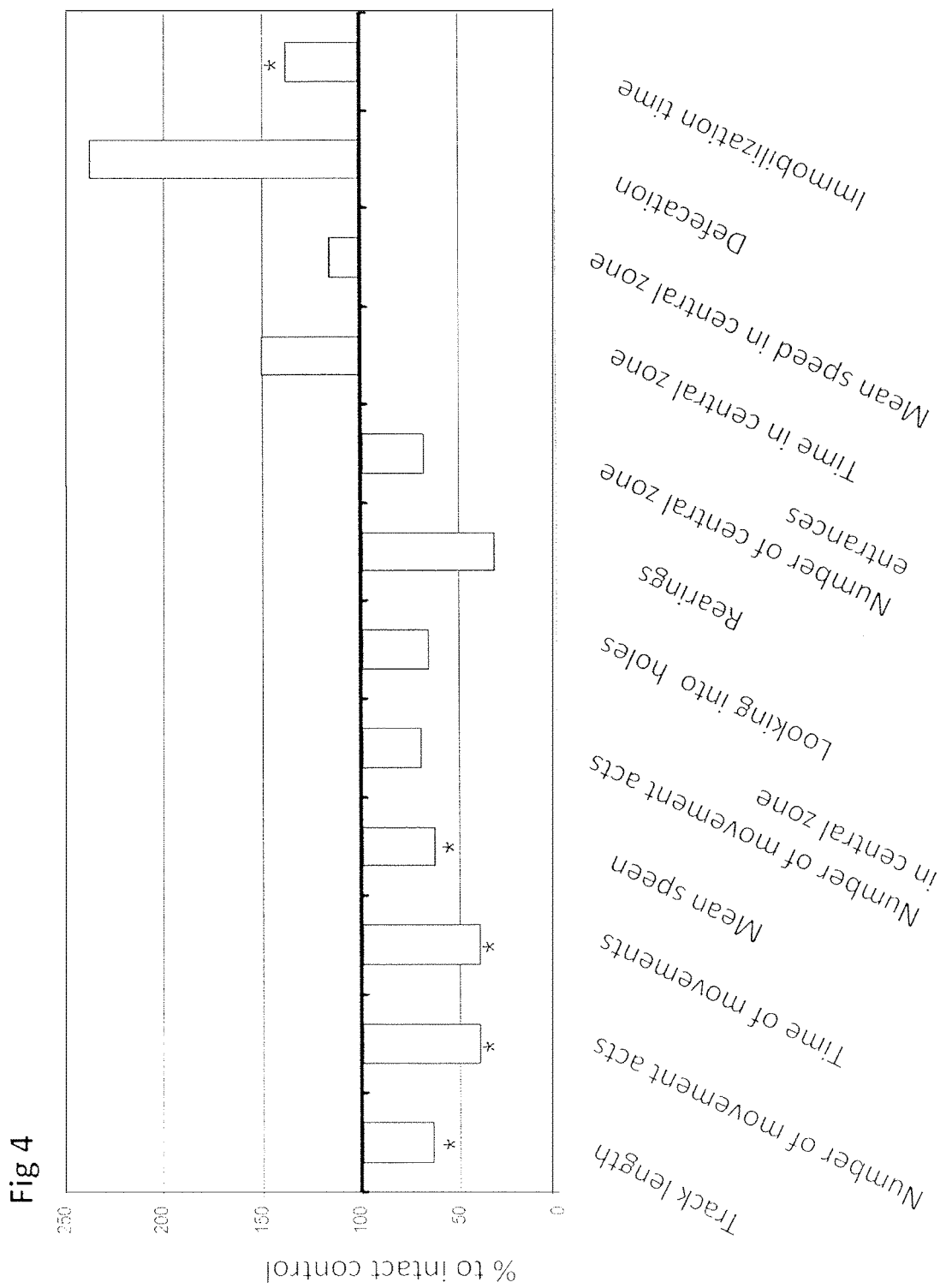

MITOCHONDRIA-TARGETED ANTIOXIDANTS FOR TREATMENT OF AGE-RELATED BRAIN DISORDERS

CROSS REFERENCE APPLICATIONS

This application is a Divisional of U.S. patent application Ser. No. 14/353,645 filed Apr. 23, 2014 which is a 371 of International Application No.: PCT/US2012/056613 filed Sep. 21, 2012 which claims the benefit of Provisional Application No. 61/537,701 filed Sep. 22, 2011, the content of which is incorporated herein by reference.

FIELD OF THE INVENTION

This disclosure is in the fields of pharmacology and medicine. More particularly, this disclosure relates to the treatment of neurodegenerative brain pathologies.

BACKGROUND

Age-related brain pathologies caused by neurodegeneration (ND), such as Alzheimer's disease (AD) and Parkinson's disease (PD), affect millions world-wide each year. Such brain pathologies are often mediated by reactive oxygen species primarily originating from mitochondria (mROS). However, although oxidative stress and mROS play a role in ND pathogenesis, this knowledge has not led to the development of an effective treatment. For example, targeting a known antioxidant (MitoQ) specifically to quench mROS has failed (Murphy, et al., *Ann. Rev. Pharmacol. Toxicol.* 47:629-656 (2007); Snow, et al., *Mov. Disord.* 25:1670-1674 (2010); Tauskela, *Drugs* 10:399-412 (2007); Lloret, et al., *J. Alzheimer's Disease*. [Epub ahead of print, PMID: 21876249 (2011)). Moreover traditional antioxidants α-tocopherol, ascorbate and α-lipoate, although safe, have been ineffective in treating AD patients (Lott, et al., *Amer. J. Med. Genet.* 155:1939-1948 (2011)). This can be partially explained by the fact that mROS normally perform several physiological functions of vital importance, and their total elimination entails death of the organism. For example, mice and rats kept in a chamber with $O_2$-free air die within three weeks (Goldstein, *Biochemistry (Mosc)* 67:161-170 (2002)).

Thus, there remains a great need for treatments for ND pathologies.

Previously, in US Patent Application Publication US 2011/0053895 ("the '895 application"), we described how mitochondria-targeted rechargeable antioxidants can be used for the prevention and treatment of cardiovascular pathologies as well as diseases and pathological conditions originating from disorders of blood circulation or oxygen supply to tissues and organs. The '895 application includes examples that show that pretreatment with SkQR1 can provide a prophylactic effect against brain hemorrhagic stroke and behavioral abnormalities caused by cerebral compression ischemia. However, to date, there has been nothing that would show or suggest a prophylactic effect of mitochondria-targeted rechargeable antioxidants against other brain pathologies or an effect in the treatment of brain pathologies generally.

SUMMARY

The inventors have discovered that mitochondria-targeted rechargeable antioxidants, including SkQ1 and SkQR1 and other compounds of formula (I) described in the '895 application as well as the functional truncated variant thereof described herein (herein collectively referred to as "SkQ mitochondria-targeted antioxidants"), can be used alone or in combination with glycolysis inhibitors to treat brain pathologies developing in elderly humans. Such brain pathologies include AD and other neurodegenerative diseases.

In accordance with this discovery, the invention comprises, in one embodiment, a method for providing to a mammal a neuroprotective effect against a brain pathology that is mediated by reactive oxygen species originating from mitochondria (mROS), the method comprising the step of administering to the mammal an SkQ mitochondria-targeted antioxidant in an amount effective to provide said neuroprotective effect, wherein the SkQ mitochondria-targeted antioxidant is administered either prophylactically to inhibit the course of the pathology or for treatment of the pathology after its onset with the exception that, where the pathology is brain trauma or stroke, the SkQ mitochondria-targeted antioxidant is administered only for treatment after onset of the pathology. In other words, the SkQ mitochondria-targeted antioxidant is not administered prophylactically where the pathology is brain trauma or stroke.

In a preferred embodiment, the brain pathology is selected from the group consisting of brain ischemia, impairment of synaptic plasticity in a hippocampus of the subject, alcohol intoxication, hyperhomocysteinemia, and brain trauma. In another preferred embodiment, the SkQ mitochondria-targeted antioxidant is selected from the group consisting of SkQ1 and SkQR1.

In a further preferred embodiment, the SkQ mitochondria-targeted antioxidant is administered to the mammal in an amount of about 1 pmole to 1 mmole per kg of body weight of the mammal per day, preferably 1 mmole/kg/day to 100 mmoles/kg/day and more preferably 10 nmoles/kg/day to 10 mmoles/kg/day.

In one embodiment, the SkQ mitochondria-targeted antioxidant may be administered to the mammal prior to an appearance in the subject of behavioral defects due to the brain pathology. In another embodiment, the SkQ mitochondria-targeted antioxidant is administered to the mammal after the mammal has contracted the brain pathology or after an appearance in the subject of behavioral defects due to the brain pathology. The SkQ mitochondria-targeted antioxidant may be administered to the mammal by any mode of administration selected from the group consisting of intradermal, intramuscular, intraperitoneal, intravenous, subcutaneous, intranasal, epidural, oral, sublingual, intracerebral, intravaginal, transdermal, rectal, by inhalation and topical.

In yet another preferred embodiment, the SkQ mitochondria-targeted antioxidant is administered to the mammal in combination with a glycolysis inhibitor. Glycolysis inhibitors that are useful in the invention include, for example, 2-deoxglucose and any other glycolysis inhibitor known in the art to inhibit, reduce, or stop glycolysis in a cancer cell. In a preferred embodiment of the invention, the glycolysis inhibitor will be used in an amount of from about 0.05 µg/kg to about 5 mg/kg of a patient's weight along with SkQ in an amount ranging from about 0.1 µg/kg to about 10 mg/kg of the patient's weight. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy can be routinely determined according to the judgment of a health-care practitioner.

In a still further embodiment of the invention there is described a pharmaceutical composition for treating a brain pathology in a mammal comprising a synergistically effective amount of SkQ mitochondria-targeted antioxidant in combination with a glycolysis inhibitor.

BRIEF DESCRIPTION OF THE DRAWINGS

The foregoing various features of the disclosure may be more fully understood from the following description, when read together with the accompanying drawings.

FIG. 4 is a graphic representation of behavior parameters in the open field test 4 hours after ethanol narcosis of a Negative Control group in % to intact control. (*–$p<0.05$);

DESCRIPTION

Throughout this application, various patents, patent applications, and publications are referenced, either by including a citation to the patents, applications or publications in the body of the specification, including the Background or by including a footnote that corresponds to a publication in the list of references provided on the last page of the specification. The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

Prior to the detailed description of the invention which follows, one should understand that the invention is not limited to the particular methodology, protocols, and reagents described here, as they are subject to change. In addition, it should be understood that in the present invention, the terminology is used to describe particular embodiments only and does not limit the scope of the present invention which will be limited only by the appended claims. Unless otherwise specified, all technical and scientific terms used here have the same meanings that are understandable to those skilled in the art. With specific reference to the term "brain pathology", the same shall be considered to include brain disorders and abnormalities, including but not limited to those described and exemplified herein.

1. Antioxidants

In the present disclosure, SkQ mitochondria-targeted antioxidants are used to treat age-related brain disorders. For example, plastoquinonyl decyltriphenyl-phosphonium (SkQ1) and plastoquinonyl decylrhodamine 19 (SkQR1) have been used as described herein to study their effect on brain function. The general formula of SkQ is described in the '895 application and WO 2007046729. Other variants of SkQ, including plastoquinone or methylplastoquinone, conjugated with lipophillic moiety, are also useful for this purpose.

In the present disclosure, the following truncated SkQ variant ("$C_{12}TPP$") is included in the SkQ mitochondria-targeted antioxidants that may also be used to provide the described neuro-protective effects.

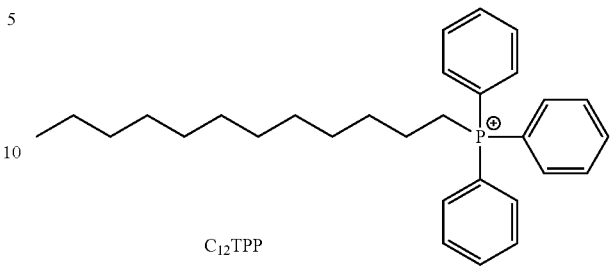

$C_{12}TPP$

2. In Vivo Studies—Effects on Ischemia

Figure 1A:
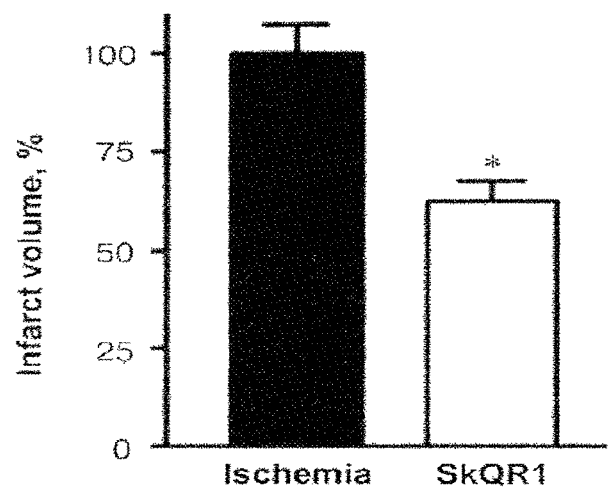
FIG. 1A is a graphic representation demonstrating that SkQR1 lowers brain infarct volume measured by staining of brain sections with 2,3,5-triphenyl tetrazolium chloride.

Several effects of SkQs were observed when brain functions were studied. Where indicated, 1 μmol SkQR1 per kg of body weight was injected intraperitoneally 24 h before the 60 min occlusion of the artery. The ischemia effect was studied 24 h after the occlusion (Plotnikov, et al., *Biochemistry (Mosc)* 75:145-150 (2010) here and below, p<0.05 for SkQ effect). In particular, a single intraperitoneal injection of SkQR1 (0.5-2 μmol/kg body weight) to rats strongly decreased the infarct volume in brain (FIG. 1A).

SkQR1 also decreased related behavioral defects caused by transient occlusion of the middle cerebral artery. Behavioral tests were performed 1 day before the induction of ischemia and on the first day after the induction of ischemia. The limb-placing test was used to evaluate the neurological deficit estimated by a conventional 14-point scale with modifications as described in Jolkkonen, et al., *Eur. J. Pharmacol.*, 400:211-219 (2000)). The test had 7 limb-placing tasks that assess the sensorimotor integration of forelimb and hindlimb responses to tactile and proprioceptive stimulation. The task was scored in a following way: the rat performed normally, 2 points; the rat performed with a delay exceeding 2 sec, and/or incompletely, 1 point; and the

Figure 1B:
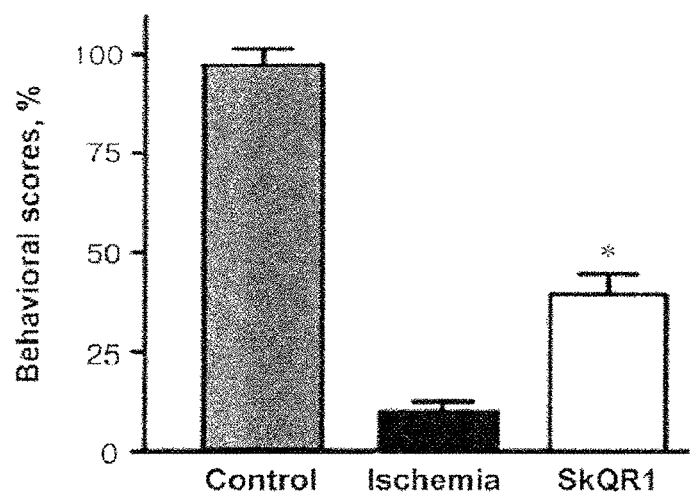
FIG. 1B is a graphic representation demonstrating that SkQR1 lowers damage to the performance of the limb placement test in rats after transient middle cerebral artery occlusion.

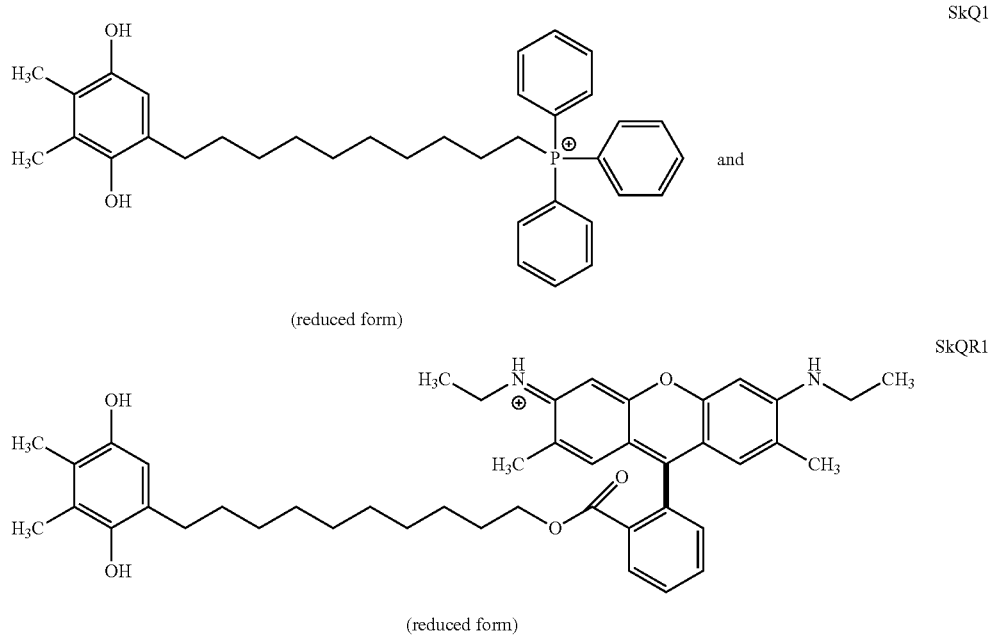

rat which did not perform normally, 0 points. FIG. 1B shows a decrease in these behavioral defects after injection of SkQR1.

Figure 2A:
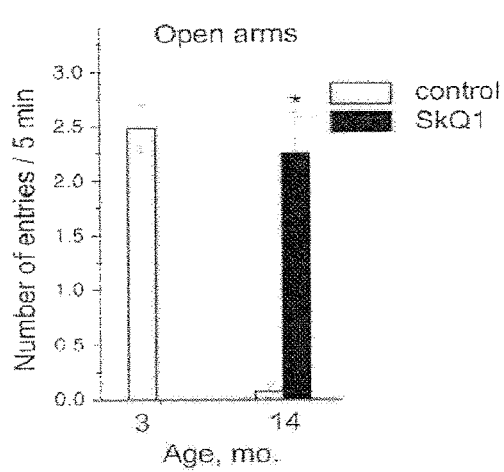
FIG. 2A is a graphic representation demonstrating SkQ1 reversal of age-dependent behavioral defects in Wistar rats as measured by the elevated plus maze (EPM), where the average number of entries into open arms of EPM is shown for young rats (3 months old, column marked with 3) and older rats (14 months old, columns marked with 14)—control (white column) and SkQ1 treated (black column).
Figure 2B:
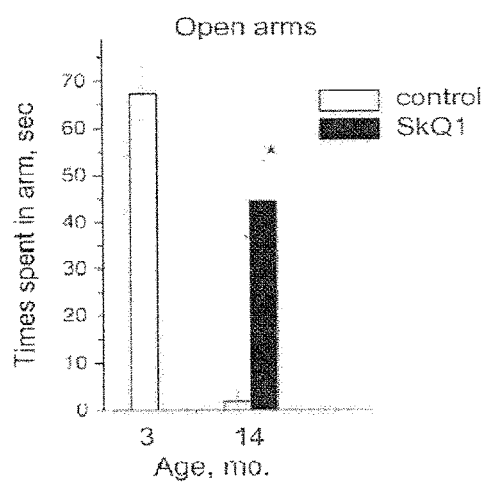
FIG. 2B is a graphic representation demonstrating SkQ1 reversal of age-dependent behavioral defects in Wistar rats as measured by the elevated plus maze (EPM), where the average time spent into open arms of EPM is shown for young rats (3 months old, column marked with 3) and older rats (14 months old, columns marked with 14)—control (white column) and SkQ1 treated (black column).
Figure 2C:
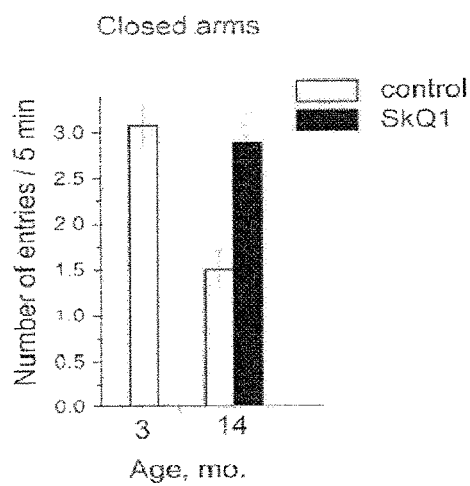
FIG. 2C is a graphic representation demonstrating SkQ1 reversal of age-dependent behavioral defects in Wistar rats as measured by the elevated plus maze (EPM), where the average number of entries into closed arms of EPM is shown for young rats (3 months old, column marked with 3) and older rats (14 months old, columns marked with 14)—control (white column) and SkQ1 treated (black column).
Figure 2D:
FIG. 2D shows average time spent into closed arms of EPM for young rats (3 months old, column marked with 3) and older rats (14 months old, columns marked with 14)—control (white column) and SkQ1 treated (black column).

A demonstrative effect of in vivo treatment with SkQ1 was observed (Stefanova, et al., *J. Alzheimer's Dis.* 21:479-491 (2010)) where age-dependant behavioral effects were studied in Wistar rats. Rats of 3 months and 14 months old were investigated. An elevated plus maze with two open and two closed arms was used. Young animals placed in the maze center entered both types of arms with equal probability (FIGS. 2A and 2C). However, the 14-month-old rats preferred to enter the closed arms only (FIG. 2D), the probability of entering the open arms being extremely low. If, nevertheless, a 14-month-old rat entered an open arm, the animal immediately left this arm (FIG. 2B). Addition of SkQ1 to the food (250 nmol/kg body weight daily) for 10 weeks completely reversed the age effect (FIG. 2D). With SkQ1, the probability of entering an open arm for the 14-month-old rats was as high as for young rats and, when entering an open arm, the SkQ1-treated old rats spent in it a time which was almost as long as for the young rodents. Number of squares crossed by the animals in the open field test proved to be slightly smaller (by 25%) for the 14-month-old rats than for the 3-month-old animals. This difference was also abolished by SkQ1 (Stefanova, et al., *J. Alzheimer's Dis.* 21:479-491 (2010)).

3. In Vivo/In Vitro Studies—Effects on Synaptic Plasticity

One of the key events in the development of AD is the release of amyloid 3 peptide (Aβ) from its protein precursor (APP) (Pagani, et al., *Int. J. Alzheimer's Dis.* 925050 (2011)). Impairment of synaptic plasticity occurs before apoptotic and neurodegenerative events typical for the terminal stage of AD. It correlates with accumulation of Aβ, causing the synaptic dysfunction and loss of memory accompanying AD (Selkoe, *Science* 298:789-791 (2002); Oddo, et al., *Neuron* 39:409-421 (2003); Haass, et al., *Nat. Rev. Mol. Cell Biol.* 8:101-112 (2007)).

Figure 3A:
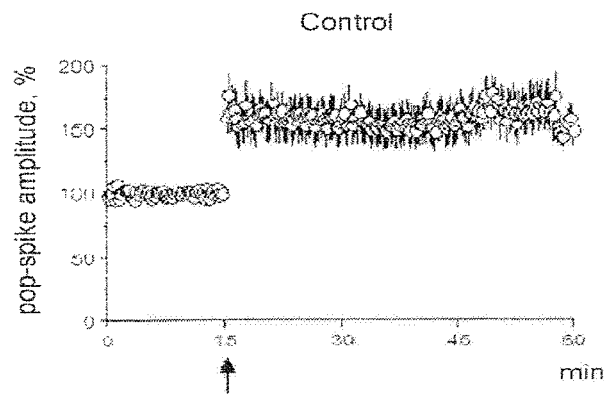
FIG. 3A is a graphic representation showing long term potentiation (LTP) of hippocampal slice neurons characterized by time course of pop-spike amplitude (%) in a control (non-treated) hippocampal slice.
Figure 3B:
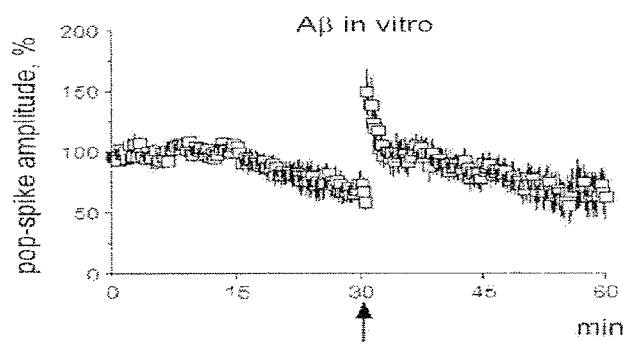
FIG. 3B is a graphic representation showing the LTP caused by in vitro addition of A$\beta$, where the decay of LTP of hippocampal slice neurons characterized by a decrease of pop-spike amplitude (%) in a hippocampal slice treated with A$\beta$.
Figure 3C:
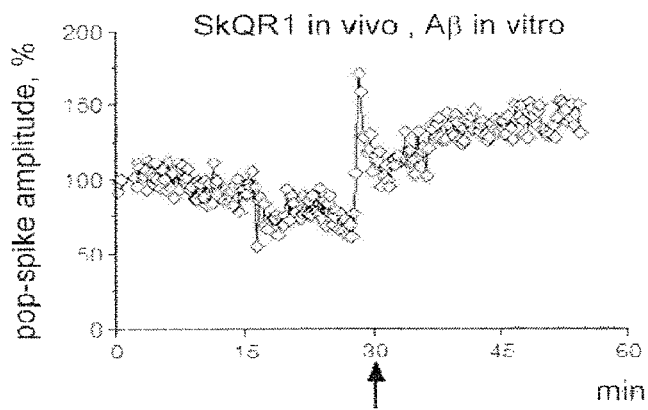
FIG. 3C is a graphic representation demonstrating that SkQR1 treatment in vivo prevents decay of the long-term potentiation (LTP) caused by in vitro addition of A$\beta$ to a hippocampal slice. SkQR1 A$\beta$ was added 15 min before the LTP induction with high-frequency electric stimulation (arrow). The decay of LTP (i.e. decrease of pop-spike amplitude) in a hippocampal slice treated with A$\beta$ can be prevented by SkQR1 treatment.
Figure 3D:
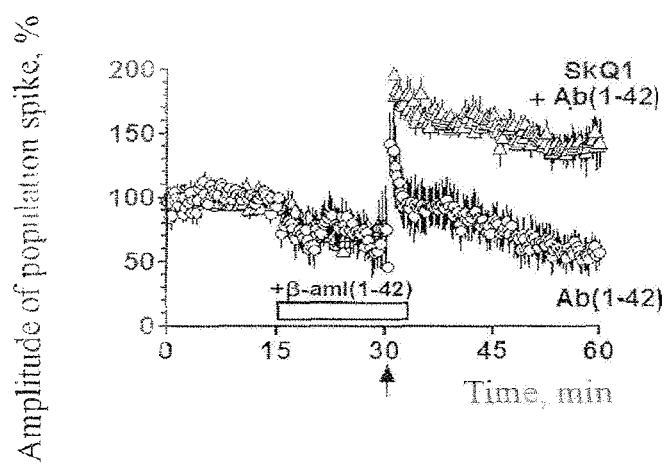
FIG. 3D is a graphic representation demonstrating that SkQ1 treatment in vivo prevents decay of the long-term potentiation (LTP) caused by in vitro addition of A$\beta$ to a hippocampal slice. SkQR1 A$\beta$ was added 15 min before the LTP induction with high-frequency electric stimulation (arrow). The decay of LTP (i.e. decrease of pop-spike amplitude) in a hippocampal slice treated with A$\beta$ can be prevented by SkQR1 treatment.

As a model of cell memory, an electric response of a hippocampal slice (long-term potentiation, LTP) was used (Malenka, et al., *Science* 285:1870-1874 (1999)). A direct experiment was performed showing the prevention of Aβ toxicity in hippocampus by in vivo treatment of rats with 1 μmol SkQR1 per kg of body weight. The compound was injected intraperitoneally into the animal 24 hours before hippocampal slices were obtained to measure LTP. Some slices were pretreated with Aβ for 15 minutes. As is seen in FIG. 3B, Aβ impaired LTP relative to untreated control. However, treatment of the animal with SkQR1 prevented such impairment (FIG. 3C).

These results show that mitochondria-targeted rechargeable antioxidants of SkQ type are useful for the treatment of AD and other mROS-mediated brain pathologies.

Figure 15:
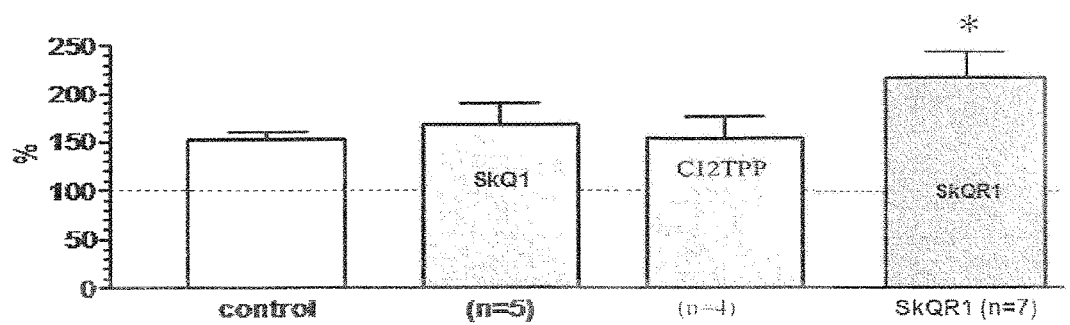
FIG. 15 is a bar graph showing the nootropic activity of preferred SkQ mitochondria-targeted antioxidants of the invention when administered to animals in vivo.
Figure 16:
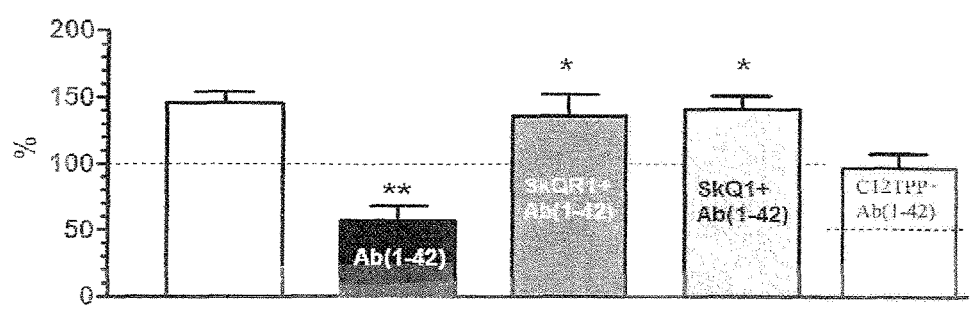
FIG. 16 is a bar graph comparing the neuroprotective effects of preferred SkQ mitochondria-targeted antioxidants of the invention when administered in vivo in a model of Alzheimer disease.

Other experiments were done that show that SkQR1 demonstrates nootropic activity when administered to animals in vivo (FIG. 15) and that all types of tested SkQs and $C_{12}TPP$ demonstrate neuroprotective activity when administered in vivo in the model of Alzheimer disease (FIG. 16). Specifically, FIG. 15 shows the nootropic effect of SkQR1 using LTP signal in neurons of hippocampal slices. As shown in FIG. 15, SkQR1 clearly stimulates LTP indicating nootropic activity of SkQ.

FIG. 16 provides a comparison of the neuroprotective effects of SkQ1, SkQR1 and $C_{12}TPP$ based on the LTP signal in neurons of hippocampal slices. Ab stands for beta-amyloid treatment. The experiment showed neuroprotective activity of SkQ1, SkQR1 and $C_{12}TPP$ in the model of Alzheimer disease. All SkQs and $C_{12}TPP$ were administered in vivo to rats prior the extraction of hippocampus. The results show that $C_{12}TPP$ exhibits lower but still sufficient neuroprotective activity compared to SkQ.

4. Neuroprotective Effect of MTA Formulations on Alcoholism and Alcohol Abuse

In alcoholism treatment the procedures used can be divided into two steps:
detoxification during alcohol deprivation; and reduction of alcohol motivation to prevent alcohol relapse.

In these experiments, 6 groups of experimental animals (Wistar rats) were used. (1) The Intact Control group (n=12), had no ethanol narcosis, and were orally administered a normal isotonic 0.90/% NaCl solution; (2) the Negative Control group (n=12) was orally administered a normal physiological solution after ethanol narcosis; (3) The SkQ1 50 nM control group (n=12) was orally administered SkQ1 in a concentration 50 nM after ethanol narcosis; (4) The SkQ1 250 nM control group (n=12) was orally administered SkQ1 in a concentration of 250 nM after ethanol narcosis; (5) The SkQ1 1250 nM control group (n=12) was orally administered SkQ1 in a concentration of 1250 nM after ethanol narcosis; (6) the SkQ1 1250 nM intr control group (n=13) was intraperitoneally administered SkQ1 in a concentration of 1250 nM after ethanol narcosis.

Figure 5:
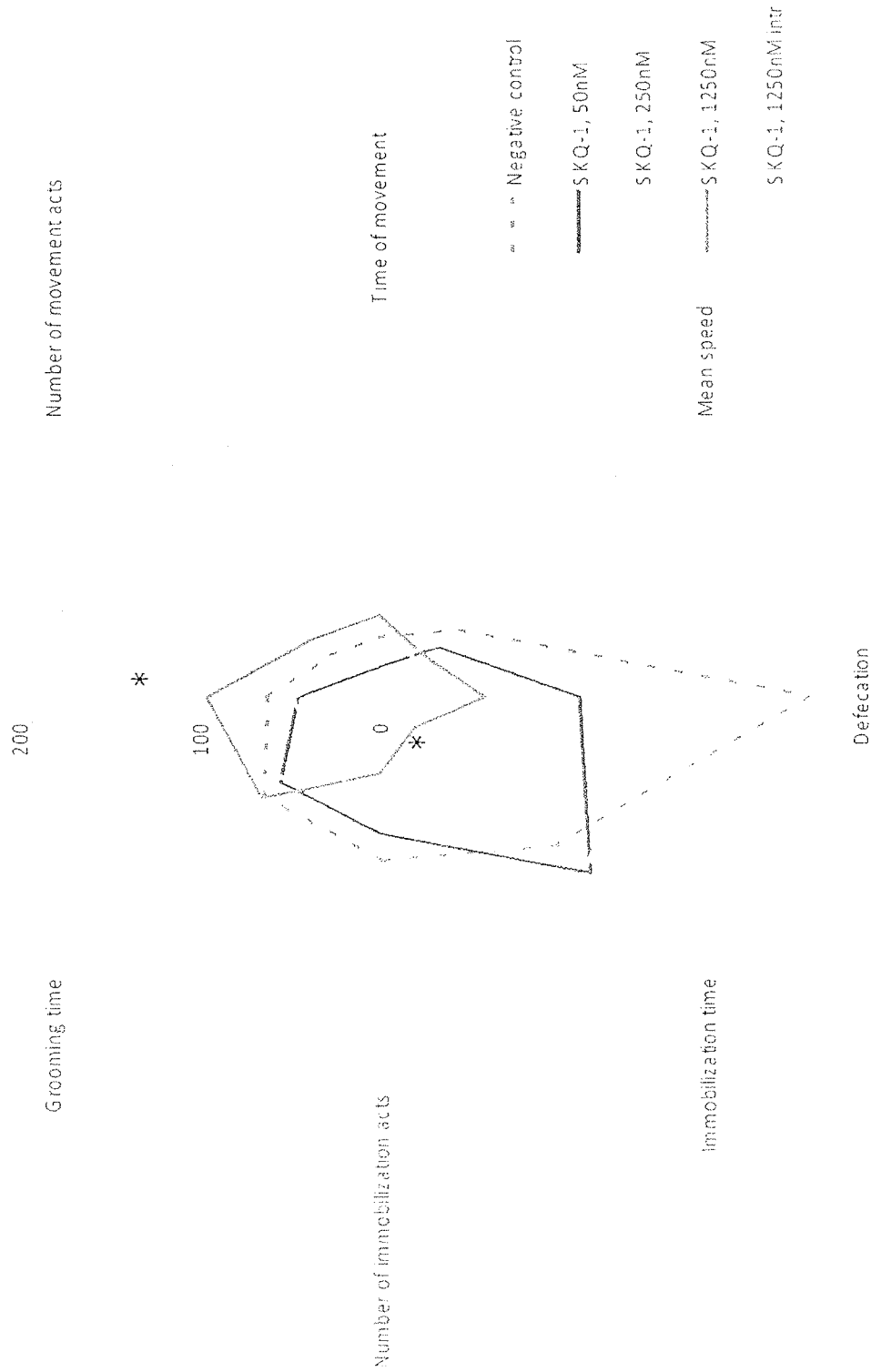
FIG. 5 is a schematic representation of the behavior parameters in the open field test 4 hours after ethanol narcosis of all groups in % to intact control. (*–$p<0.05$ for SKQ-1 250 nM compared to negative control)
Figure 6:
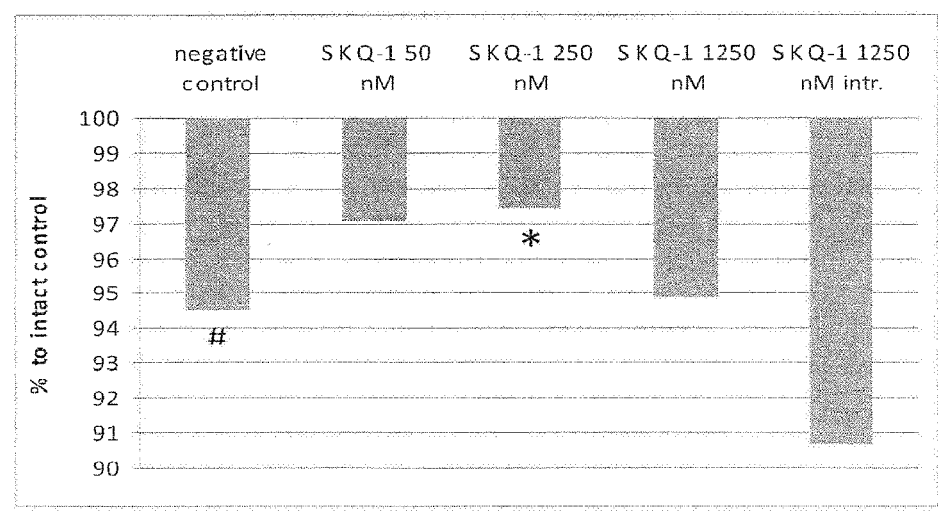
FIG. 6 is a graphic representation showing muscle strength measurement 4 hours after ethanol narcosis in % to intact control. *–$p<0.05$ to negative control, #–$p<0.05$ to intact control.

Four hours after awakening from ethanol narcosis, acute symptoms of ethanol intoxication were observed in an open field test. In the Negative Control group ethanol intoxication caused a decrease of locomotor activity compared to Intact Control group: decreased track length (p<0.05), movement time (p<0.05), mean speed (p<0.05) and increased immobilization time (p<0.05) (FIG. 4). The 250 nM SkQ1 dose had the most pronounced effect, increasing track length (p<0.05), decreasing immobilization time (p<0.05) (FIG. 5). Ethanol intoxication caused muscle weakness (p<0.05) in the Negative Control group. Administration of SkQ1 250 nM reduced this effect, increasing muscle strength (p<0.05) (FIG. 6).

Figure 7:
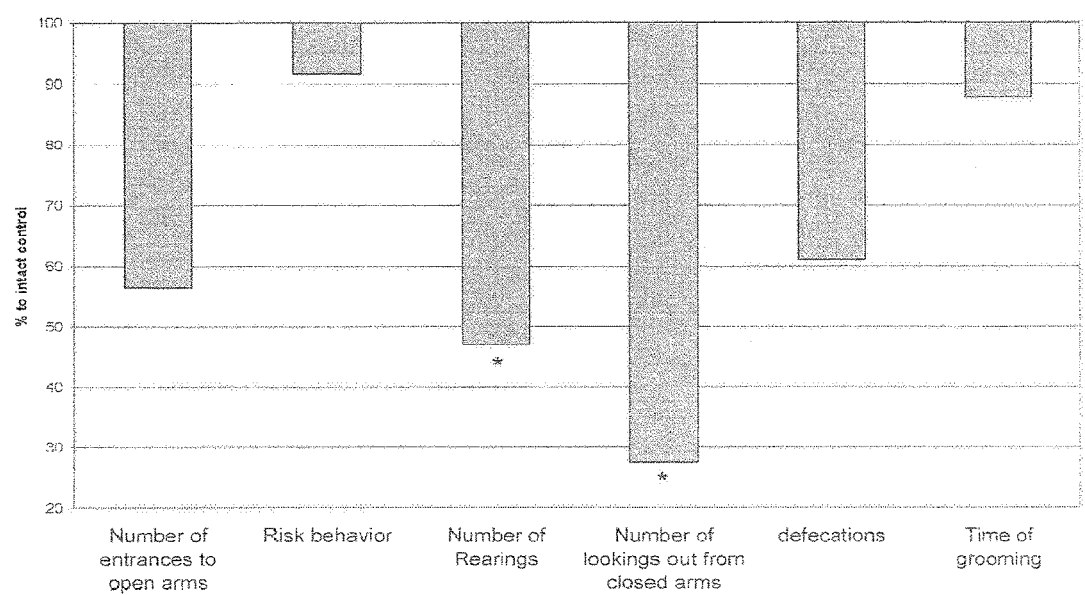
FIG. 7 is a graphic representation showing behavior parameters in the elevated plus maze test 24 hours after ethanol narcosis of Negative Control group in % to intact control. (*–$p<0.05$)
Figure 8:
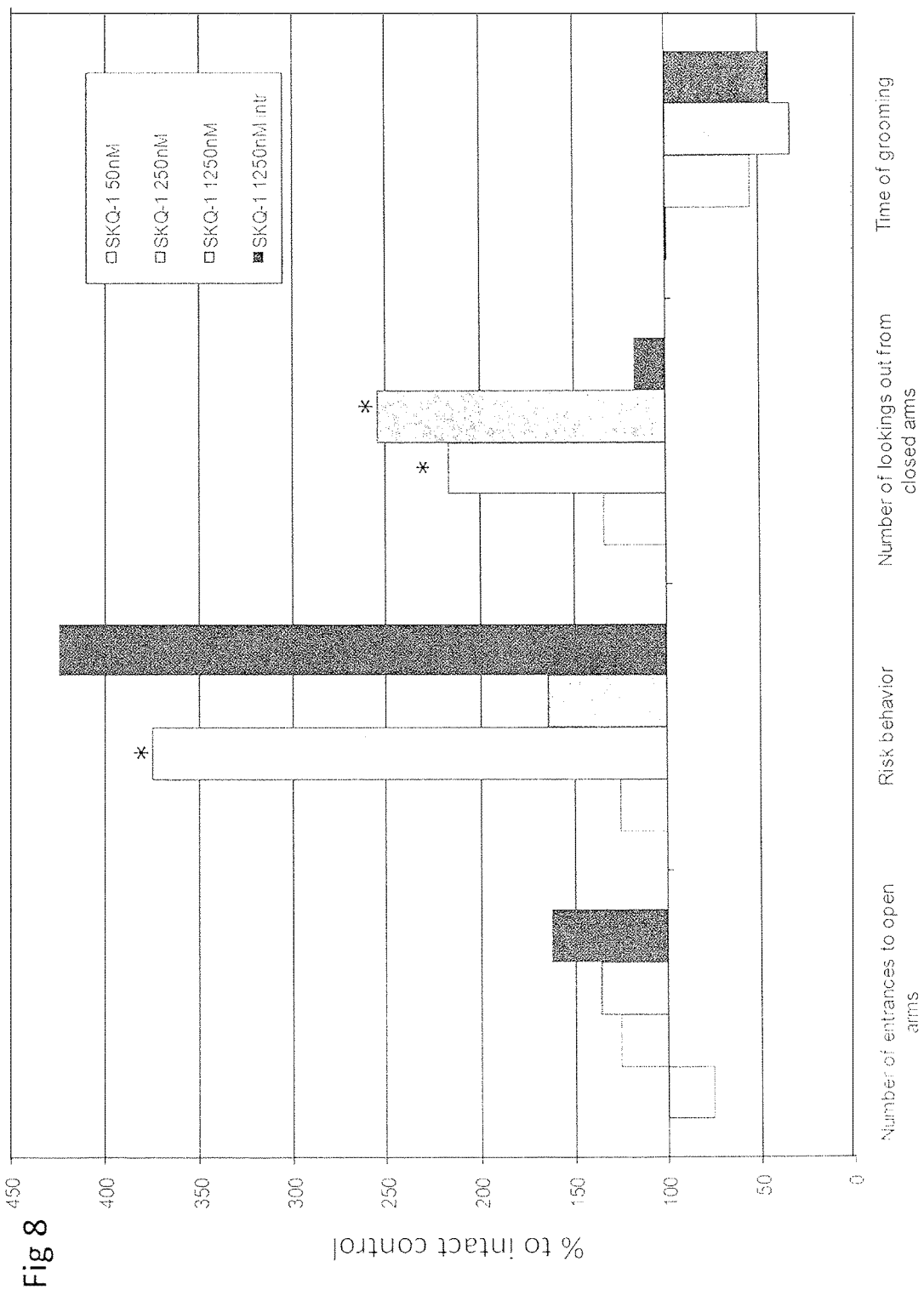
FIG. 8 is a graphic representation showing behavior parameters in the elevated plus maze test 24 hours after ethanol narcosis in % to negative control. (*–$p<0.05$ to intact control)

Twenty-four hours after ethanol narcosis, elevated plus maze (Treit et al. (1993) *Pharmacol. Biochem. Behav.* 44:463-9) and Porsolt forced swimming (Petit-Demouliere et al. (2005) *Psychopharmacol.* (*Berl*). 177: 245-55) tests were performed. In the elevated plus maze test, ethanol intoxication caused decrease of exploratory activity, resulting in lower number of rearing (p<0.05) and looking out from closed arms p<0.05) in the Negative Control group compared to the Intact Control (FIG. 7). In the 250 nM SkQ1 group, the level of exploratory activity is higher: increased number of risk behavior (p<0.05), looking out from closed arms (p<0.05) (FIG. 8).

Thus, a single dose of mitochondrial antioxidant SkQ1 after ethanol narcosis improved behavioral and physiological parameters, alleviating acute alcohol intoxication. SkQ1 also had pronounced effect on chronically alcoholised rat.

Male albino rats had free access to a 15% ethanol solution, as well as to food and water. After 6 months of alcoholisation, animals with average consumption more than 11 ml of 15% ethanol solution were divided into two even groups and subjected to the following treatment. The Negative Control group (n=16) (chronically alcoholised rats) were orally administered 1 ml per kg of isotonic 0.9% NaCl solution every two days for 20 days during alcohol deprivation. The SkQ1 group (n=17) (chronically alcoholised rats) were orally administered 1 ml per kg of SkQ1 250 nM solution every two days for 20 days during alcohol deprivation. The Intact Control group (n=10) (animals had no previous contact with ethanol) were orally administered 1 ml per kg of normal physiological solution every two days for 20 days.

After this course of drug administration, the effect on behavioral parameters was observed using the open field test, the elevated plus maze test, and the Porsolt forced swimming test.

Figure 9:
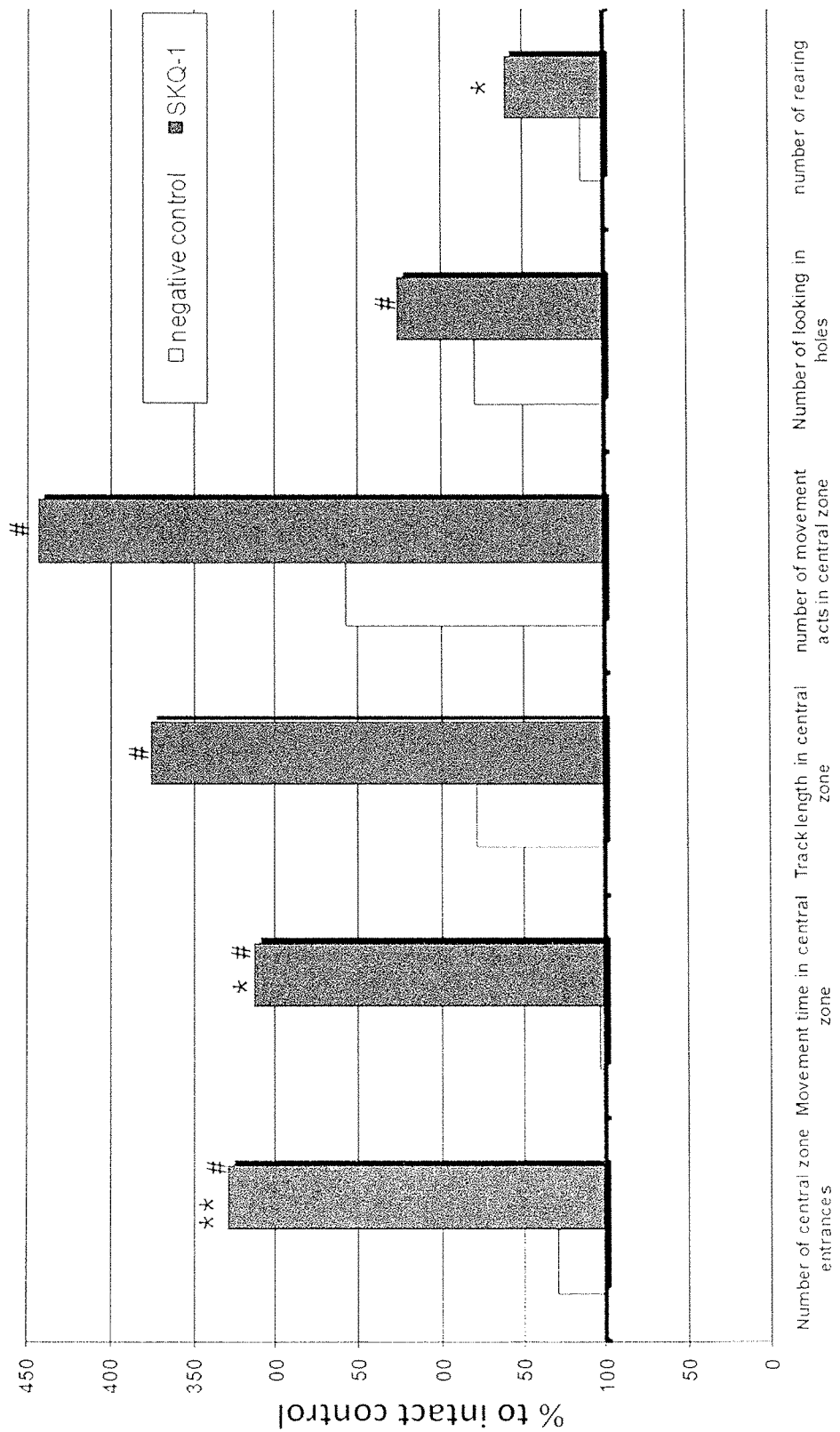
FIG. 9 is a graphic representation showing behavior parameters in the open field test of chronically alcoholised rats in % to intact control. (*–$p<0.05$; **–$p<0.005$ to negative control; #–$p<0.05$, ##–$p<0.01$, to intact control)

In the open field test, treated animals had increased number of rearing (($p<0.05$), number of entrance in central zone ($p<0.01$), movement time in central zone ($p<0.05$)) compared to the Negative Control group (FIG. 9. Therefore, SkQ1 increases exploratory activity during alcohol deprivation.

Figure 10:
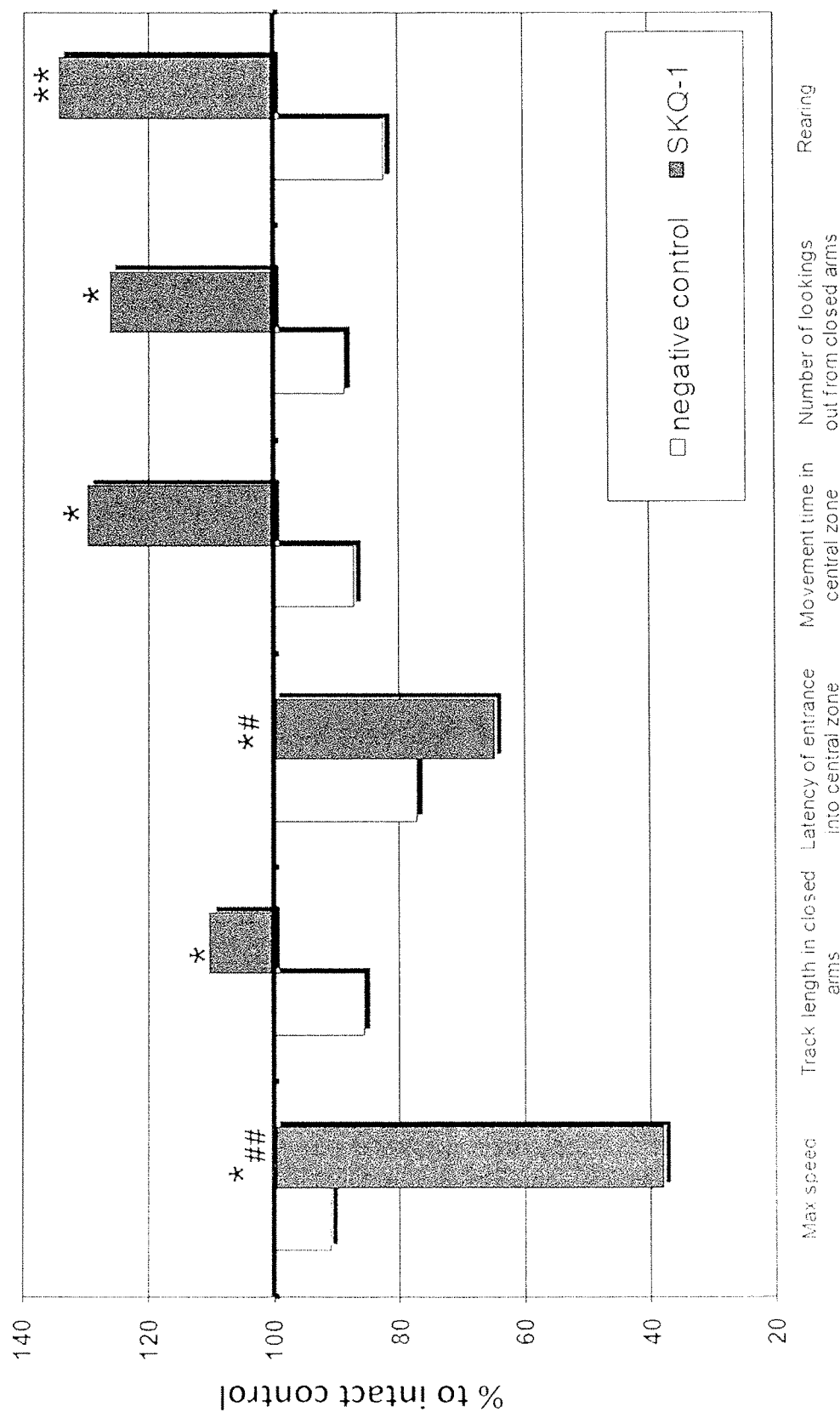
FIG. 10 is a graphic representation showing behavior parameters in the elevated plus-maze test of chronically alcoholised rats in % to intact control. (*–$p<0.05$; **–$p<0.005$ to negative control; #–$p<0.05$, ##–$p<0.01$, to intact control)

In the elevated plus maze test, the SkQ1 group had an increased track length in closed arms (($p<0.05$), movement time in central zone ($p<0.05$), number of looking out from closed arms, rearing ($p<0.005$)) compared to the Negative Control group (FIG. 10. This is indicative of lower anxiety in the SkQ1 group.

Figure 11:
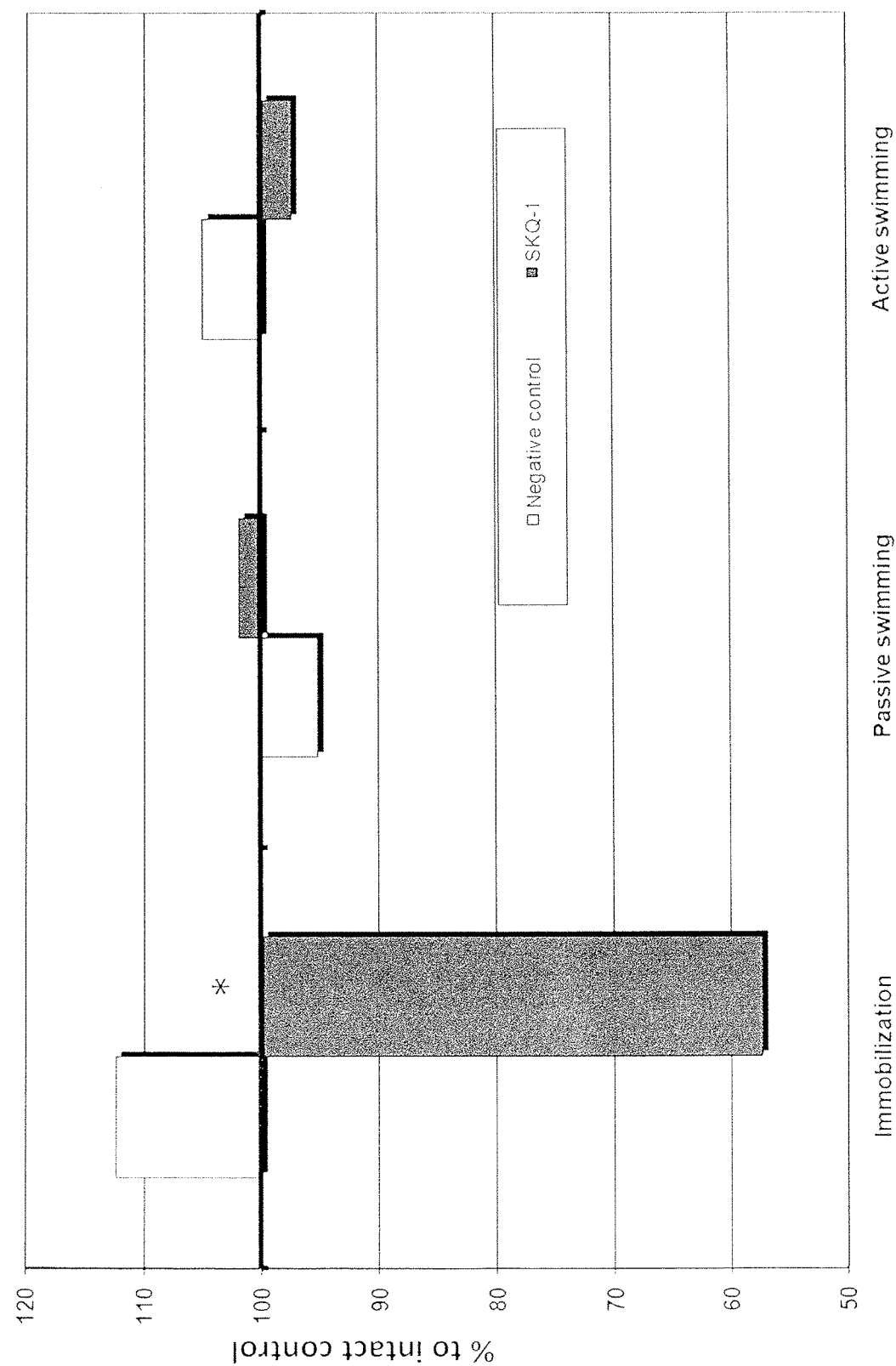
FIG. 11 is a graphic representation showing behavior parameters in the Porsolt forced swimming test of chronically alcoholised rats in % to intact control. (*–$p<0.05$ SKQ-1 to negative control)

The forced swimming test showed a decrease of depression parameters; animals of the SkQ1 group had less immobilization time ($p<0.05$) (FIG. 11).

According to behavioral tests, administration of SkQ1 during alcohol deprivation can alleviate ethanol withdrawal symptoms: increasing exploratory activity, without hyperactivation of locomotor activity; and decreasing anxiety and depression components in behavior.

Figure 12:
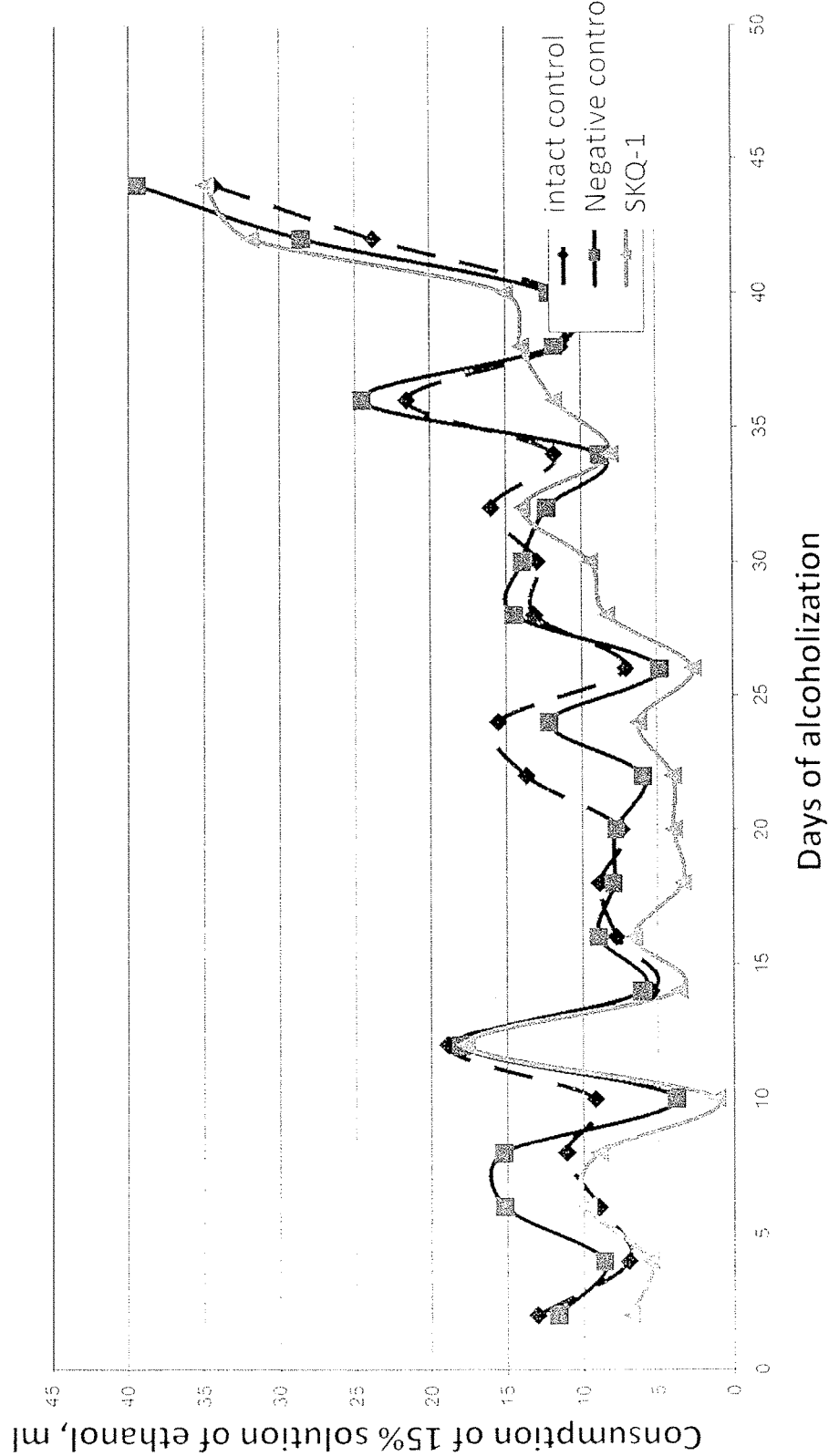
FIG. 12 is a graphic representation showing the consumption of 15% ethanol solution after deprivation in ml (*–$p<0.01$ on 1st day of alcoholisation SKQ-1 to negative control; #–$p<0.05$ for average ethanol consumption for 1-36 days SKQ-1 to negative control).

After behavioral testing, ethanol consumption of 15% solution was measured for 45 days. The level of ethanol consumption during first day in the SkQ1 group was lower ($p<0.01$) than in the Negative Control group. The decreased ethanol consumption during first day indicates lower level of ethanol craving after SkQ1 administration. During the next month, the average ethanol consumption was nearly 2× lower ($p<0.05$) in the SkQ1 group than in the Negative Control group (FIG. 12). Additionally, the body weight of rats after SkQ1 administration was higher ($p<0.05$).

Therefore, SkQ1 had pronounced effect on chronically alcoholised rat, decreasing ethanol consumption twice and improving behavior parameters during alcohol deprivation without any correlation with individual behavior parameters: increasing exploratory activity and decreasing depression.

This data contains evidence that a mitochondrially targeted antioxidant has neuroprotective activity in vivo. Such activity can be used for creation of a treatment of alcohol abuse and alcoholism and other conditions related to damage of nervous system, including withdrawal syndrome.

The present disclosure utilizes mitochondrial antioxidants to treat alcohol intoxication and abuse. The disclosure provides a procedure to treat alcoholic patient with therapeutically-efficient doses of mitochondrial-targeted antioxidant in order to decrease the damage done by alcohol and it derivates and to reduce alcohol dependency of the patient.

Administration of SkQ1 can be used in combination with basic alcohol therapy. Exemplary modes of basic therapy used in a period of abstinence include, but are not limited to, administration of sedatives, anticonvulsants, vitamins, electrolyte repletion, antidepressants, and psychotherapy. Doses of all drugs are individual, as well as additional treatment, according to patient condition and co-occurring medical problems.

5. Neuroprotective Effect of MTA Formulations on Homocysteine-Induced Brain Damage Hyperhomocysteinemia is associated with several neurodegenerative disorders where glutamate receptors of modulators of glutamate receptors are involved, such as Alzheimer's disease, schizophrenia. In adults hyperhomocysteinemia can cause cerebral aneurisms (Xu, et al. (2011) *Neurosci. Lett.*, 494:139-44), pulmonary embolism (Karalezli, et al. (2011) *Clin. Appl. Thromb. Hemost. Epub ahead of print*), Crohn's disease (Maire, et al. (2001) *Gastroenterol. Clin. Biol.*, 25: 745-8), non alcoholic fatty liver disease (Bravo, et al. (2011) *Lipids Health Dis.*, 10:60), dementia and Alzheimer's disease (Deshmukh, et al. (2010) *Eur. J. Clin. Nutr.*, 64: 495-502], vascular dementia, cognitive impairment or silent or asymptomatic embolic stroke, (Herrmann, et al. (2011) *Clin. Chem. Lab. Med.*, 49: 435-41), brain atrophy in patients with brain epilepsy (Gorgone, et al. (2009) *Epilepsia, Suppl.* 1:33-6), atherosclerosis and thrombophilia (Kolling et al. (2011) *Cardiovasc. Toxicol.* 11:67-73).

Hyperhomocysteinemia during pregnancy can cause preeclampsia, intrauterine growth retardation, premature rupture of the membranes, placental abruption (Murphy, et al. (2011) *Adv. Clin. Chem.*, 53: 105-37], early miscarriage (Vollset, et al. (2000) *Am. J. Clin. Nutr.*, 71:962-8), gestosis (late toxicosis) (Azizi, et al. (2010) *Bone*, 46:1344-8), neurocognitive impairment in children (Bhate et al. (2008) *Food Nutr. Bull.*, 29:249-54), microcephalia, megaloblastic anaemia, and hypotonia (Honzik, et al. (2010) *J. Paediatr. Neurol.*, 14: 488-95), neural tube defects (Rogers (2008) *Med. Hpotheses.*, 71: 406-10), hypotrophy (Molloy, et al. (2009) *Pediatrics.*, 123: 917-23), and Down's syndrome (Murphy, et al. (2011) *Adv. Clin. Chem.*, 53: 105-37).

An experiment was performed on 161 female Wistar rats (n=12) with body weight 200 g-250 g and their offspring (n=149) from 0 to 1.5 months old. All animals were SPF-category and were housed under the standard conditions according to GLP-regulations (controlled microbiological conditions, light-dark cycle 12/12 hours, ventilation rate 10-12 V/h, room temperature 22+2° C., with maximum change 1° C. per day, humidity 30-70%). Rats were housed in individual cages with free access to food and water.

Each female rat was held with 3 male rats for one night. First day of the pregnancy was considered to be the day when spermatozoon were found in a vaginal smear. Hyperhomocysteinemia is experimentally developed by oral administration of L-methionine (Makhro, et al. (2008) *Bull. Expt. Biol. Med.*, 146:37-39). L-methionine was added to the drinking water of rats at the dose of 1 mg/kg of body weight per day for whole period of pregnancy (approximately 21 d). L-methionine administration was continued after offspring birth (lactation period approximately 30 d). Therefore, offspring obtained L-methionine both with mother milk and from drinking water. Females of the experimental group were orally administered SkQ1 in dose 250 nM/kg in 50 ml solution once per 2 d during period of lactation. Animals from the control group were given distilled water instead of SkQ1.

On day 45 of life, pups were tested for schizophrenia symptoms in acoustical startle reflex. Normally (on control non-hyperhomocysteinemia rats) weaker pre-impulse (70 dB white noise, stimuli sound volume 80 dB, duration 20 ms) decreases reaction on louder stimulus (70 dB white noise, stimuli sound volume 100 dB, duration 20 ms) produced in 100 ms after first signal in comparison to louder stimulus given alone. This phenomenon is called pre-impulse inhibition. In the experiment stimuli were produced 20 times with the background white noise (sound volume 70 dB). In case of schizophrenia or similar disorders in brain functions pre-impulse inhibition and adaptation to the stimuli is less pronounced or absent (Kar. et al. (2003) *Exp. Toxicol. Pathol.*, 55(1): 69-83).

Figure 13:
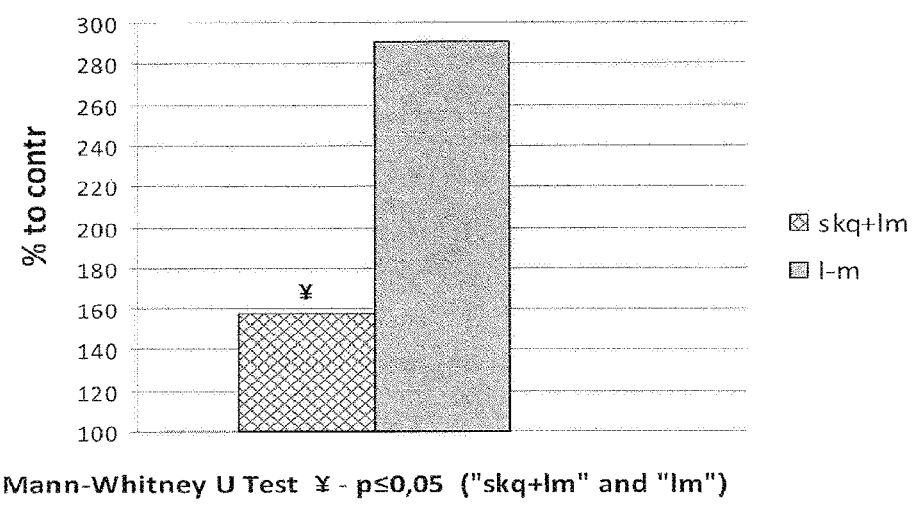
FIG. 13 is a graphic representation showing the inhibition of startle reaction to loud stimulus by pre-impulse in rats, where the histogram bars indicate the mean level of startle reaction after pre-stimulus as % to that of control group of rats (without hyperhomocisteinemia). l-m corresponds to group of rats treated with high L-methionine diet, and skq+lm corresponds to group of rats treated with high L-methionine diet and SkQ1.
Figure 14:
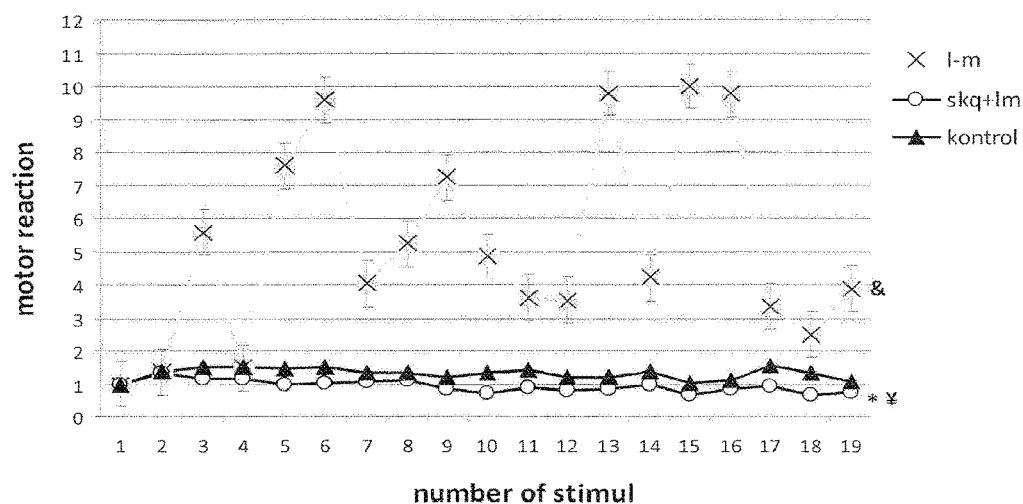
FIG. 14 is a graphic representation showing habituation of rats to double acoustic stimulus in normal conditions, under hyperhomocisteinemia and under hyperhomocisteinemia treated with SkQ1, where motor reaction to the double stimulus and P values for different pairs of groups is indicated.

The results presented in FIGS. 13 and 14 demonstrate that offspring of rats with hyperhomocisteinemia show deficit of pre-impulse inhibition (high mean level of startle reaction to loud stimulus given after pre-impulse) that indicate development of schizophrenia. SkQ-1 given to mother rats normalized parameters of pre-impulse inhibition of the progeny (FIG. 13). Rats after prenatal hyperhomocisteinemia show non stable and very high reflex reaction on sound stimuli. In SkQ1-treated group this effect of hyperhomocisteinemia was significantly reduced (FIG. 14).

6. In Vivo Studies—Effect on Trauma

In this study, we, the inventors, employed our modification of the earlier used model of focal open severe brain trauma in rats [13]. The study was performed on male Wistar rats with body weight of 180-250 g. Before the surgery, the animals were anesthetized by an intraperitoneal injection of 3% chloral hydrate (330 mg/kg). To create the trauma, the left frontal part of the skull was trepanized above the sensorimotor cortex zone, and a movable Teflon piston 4 mm in diameter with depth of insertion of 2.5 mm was placed into it; this piston was struck from the height of 10 cm with a 50-g load sliding along a directing rail. Localization of the sensorimotor cortex zone was determined based on data described in [14].

SkQR1 (100 nmol/kg) was injected intraperitoneally 1 h after the trauma and then daily in the same dose during the following four days.

A magnetic resonance imaging (MRI) study was performed as described in [15] using a BioSpec 70/30 (Bruker, Germany) with magnetic field induction of 7 T and gradient of 105 mT/m. The damaged focal volume was determined morphometrically on the 7th day after the trauma. For this, the brain of the animal was fixed by submerging it in a mixture of formalin-ethanol-acetic acid in the ratio 2:7:1 for 24 h; then the brain was placed in 70% ethanol for 24 h; then serial sections were prepared using a NVSLM1 vibratome (World Precision Instruments) with a step of 100 μm. Every second section was sequentially mounted onto glasses covered with gela_tin and stained with 0.2% Methylene Blue. Then the sections were treated routinely (dehydrated with increasing ethanol concentration, cleared with xylene, and mounted in balsam) and scanned on a slide-device of an Epson Perfection V100 PHOTO scanner. As a result, files were obtained with a picture of light-blue section of the brain with a clearly shown damage area. The volume of the lesion was determined as a cylinder with $V=\Sigma Sn \times d$, where d is thickness of the section pair (200 μm); Sn is the area of the lesion in the section in mm2; $\Sigma$ is the sum of volumes of ischemic damage in the sections using an Image J program (Bethesda Md., USA).

Behavioral "limb-placing test" was performed 24 h before the operation and then on the third and seventh days after the trauma. Neurologic deficit caused by the skull-brain trauma was estimated using a 12-score scale [16] in modification [17]. The resulting score on this scale is determined as the sum of points obtained in six tests assessing the response of the forelimbs and hindlimbs to tactile and proprioceptive stimulation in the presence of obvious reflexes. Malfunctioning of the limb was estimated using the following system: 2 points corresponds to complete performance of the test; 1 point corresponds to performing the test with a delay of 2 sec or incompletely; 0 point corresponded to the lack of response to the stimulation of the limb.

The results are expressed as the mean±standard error of mean. The results of behavioral tests were compared using the Mann-Whitney test for independent samples. The statistical significance of differences in the damaged volumes was assessed using Student's t-test at the significance level of $p<0.05$.

The animals were treated and subjected to experimental procedures in accordance with requirements of the Counsel of the European Community 86/609/EEC on use of animals for experimental studies.

Magnetic resonance images obtained on the first day after the skull-brain trauma allowed us to clearly identify the lesion area in the sensorimotor cortex of the left hemisphere. The localization of the damaged area was in complete correlation with data on behavioral performance based on the sensitivity and motor activity of the limbs.

The results of the limb-placing test revealed the development after the trauma of a functional deficit in the right limbs, whereas it was absent in the left limbs. In the intact rats before the trauma, the test gave 12 points for both the right and left limbs, and after the skull-brain trauma in the rats not treated with SkQR1 this score for the right limbs was 4.5±0.9 points on the third day (n=14) and 4.3±0.8 points on the seventh day (n=14).

The intraperitoneal injections of SkQR1 significantly decreased the neurological deficit. In this case the right limbs of the rats showed on the third day 6.6±0.8 (n=14) and 7.4±0.8 points (n=14) on the seventh day after the trauma. The morphometric analysis after completing the behavioral test revealed that on the seventh day after the trauma the injection of SkQR1 decreased the damaged volume nearly twofold (to 15±4 mm3 (n=14)), whereas without treatment with SkQR1 the damaged area was 28±4 mm3 (n=13).

Thus, in our work the injection of SkQR1 to animals after skull-brain trauma was shown for the first time to significantly decrease the neurological posttraumatic deficit and the volume of lesion.

It has been earlier shown that extremely low, nanomolar concentrations of mitochondria-targeted antioxidants, plastoquinone derivatives SkQ1 and SkQR1, could be used on animal models of various pathologies including Alzheimer's disease, cardiac arrhythmia, and myocardial and renal infarction 2009, 2008, 2010, 2011 the pathogenesis of which is significantly determined by increased production of ROS in mitochondria. On various models of ischemic brain stroke, we have demonstrated that mitochondria-targeted antioxidants are efficient in preventing the consequences of brain ischemia such as destruction of nervous tissue and neurological deficit 2008, 2010. Skull-brain trauma is another serious medical problem. In the present invention, this pathology was studied on our modified model of open focal brain trauma [13]. This model allowed to obtain a standard in the size and localization of cortical damage accompanied by pronounced neurological deficit corresponding to clinical manifestations of the brain trauma. This model improves perspectives in the search and experimental base for pharmacological correction of this cerebral pathology.

The mechanisms of development of brain trauma and brain ischemia are similar in common, and the propagation of these pathologies significantly depends on mitochondria and the MMP [11, 18], which leads to an increased production of ROS by mitochondria [10, 12]. These active molecules directly damage lipids, proteins, and nucleic acids in the cell. ROS also activate different molecular signaling pathways associated with cell death [19]. The increased production of ROS by mitochondria under conditions of both ischemia and trauma is the most important pathogenetic detail in the mechanism of the neurodestruction. Therefore, it was reasonable to suggest that the trauma-induced development of neurological distortion could be decreased using mitochondria-targeted antioxidants [20]. In the present invention, for the first time we were able to demonstrate that the injection of SkQR1 in nanomolar concentrations during four days after skull-brain trauma reliably decreases the neurological deficit, whereas in the absence of SkQR1 this deficit did not decrease during the same period. The morphometric analysis of the damaged area revealed that in the SkQR1-treated rats the volume of the lesion in the brain cortex was significantly lower than in the untreated animals. The mechanism of the protective effect can be mediated through the ability of SkQR1 to decrease the level of mitochondrial ROS and also to induce in vivo ischemic tolerance due to initiating an increased production of erythropoietin that, in turn, decreases the activity of glycogen synthase kinase (GSK-3β) [2011], which is involved in the apoptotic cascade in neurons under conditions of ischemia, trauma, and in Alzheimer's disease. Previously, there have been attempts to treat ischemia and trauma using common, non-targeted antioxidants, but their efficiency was rather limited, especially in clinical studies [22].

7. Therapeutic Administration

The route and/or mode of administration of the antioxidant-containing pharmaceutical compositions described herein can vary depending upon the desired results. One with skill in the art, i.e., a physician, is aware that routes or modes of administration, as well as regimens can be adjusted to provide the desired response, e.g., a therapeutic response.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical. The mode of administration is left to the discretion of the practitioner.

For example, in some instances, the pharmaceutical composition described herein is administered locally. This is achieved, for example, by local infusion during surgery, by injection, by means of a catheter, by means of a suppository or enema, or by means of an implant, the implant being of a porous, non-porous, or gelatinous material, including membranes, such as sialastic membranes, or fibers. In some situations, the pharmaceutical composition described herein is introduced into the central nervous system, circulatory system or gastrointestinal tract by any suitable route, including intraventricular, intrathecal injection, paraspinal injection, epidural injection, enema, and by injection adjacent to a peripheral nerve.

Pulmonary administration can also be employed, e.g., by use of an inhaler or nebulizer, and formulation with an aerosolizing agent, or via perfusion in a fluorocarbon or synthetic pulmonary surfactant.

The pharmaceutical composition described herein can be formulated to include a suitable amount of a physiologically acceptable carrier or excipient (see, e.g., *Remington's Pharmaceutical Sciences*, pp. 1447-1676 (Alfonso R. Gennaro, ed., 19th ed. 1995)). Such physiologically acceptable excipients can be, e.g., liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one situation, the physiologically acceptable excipients are sterile when administered to an animal. The physiologically acceptable excipient should be stable under the conditions of manufacture and storage and should be preserved against the contaminating action of microorganisms. Water is a particularly useful excipient when the pharmaceutical composition described herein is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Other examples of suitable physiologically acceptable excipients are described in *Remington's Pharmaceutical Sciences*, pp. 1447-1676 (Alfonso R. Gennaro, ed., 19th ed. 1995). The pharmaceutical compositions, if desired, can also contain minor amounts of wetting or emulsifying agents, or pH buffering agents.

Liquid carriers can be used in preparing solutions, suspensions, emulsions, syrups, and elixirs. The pharmaceutical composition described herein can be suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particular containing additives described herein, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. The liquid carriers can be in sterile liquid form for administration. The liquid carrier for pressurized compositions can be halogenated hydrocarbon or other pharmaceutically acceptable propellant.

In other instances, the antioxidant-containing pharmaceutical composition described herein is formulated for intravenous administration. Compositions for intravenous administration can comprise a sterile isotonic aqueous buffer. The compositions can also include a solubilizing agent. Compositions for intravenous administration can optionally include a local anesthetic such as lignocaine to lessen pain at the site of the injection. The glycolytic enzyme or the glycolytic enzyme and the mitochondrially-targeted antioxidant can be supplied either separately or mixed together in unit dosage form, for example, as a concentrate in a hermetically sealed container such as an ampoule or sachette indicating the quantity of active agent. Where the pharmaceutical composition described herein is administered by infusion, it can be dispensed, for example, with an infusion bottle containing sterile pharmaceutical grade water or saline. Where the pharmaceutical composition described herein is administered by injection, an ampoule of sterile water for injection or saline can be provided so that the enzyme or enzyme and antioxidant and the carrier can be mixed prior to administration.

The amount of antioxidant-containing pharmaceutical composition described herein that is effective for treating an ND can be determined using standard clinical techniques known to those with skill in the art. In addition, in vitro or in vivo assays can optionally be employed to help identify optimal dosage ranges. The precise dose to be employed can also depend on the route of administration, the ND, the seriousness of the ND being treated, as well as various physical factors related to the individual being treated, and can be decided according to the judgment of a health-care practitioner. For example, an antioxidant or glycolysis inhibitor in an amount of from about 0.05 µg/kg to about 5 mg/kg of a patient's weight can be used. An antioxidant in an amount ranging from about 0.1 µg/kg to about 10 mg/kg of a patient's weight can be used. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy can be determined according to the judgment of a health-care practitioner.

In some instances, the pharmaceutical composition described herein is in unit dosage form, e.g., as a tablet, capsule, solution, suspension, emulsion, or granule. In such form, the pharmaceutical composition can be sub-divided into unit doses containing appropriate quantities of the pharmaceutical composition described herein. The unit dosage form can be a packaged pharmaceutical composition, for example, vials, ampoules, pre-filled syringes or sachets containing liquids.

One exemplary pharmaceutical composition comprises SkQ1 and 3PO. For example, SKQ1 in amounts ranging from about 0.05 µg/kg to about 5000 µg/kg of patient's weight and 3PO in amounts ranging from about 0.0001 mg/kg to about 10 mg/kg of patient's weight are useful in this pharmaceutical composition.

Another useful treatment of ND is to administer an SkQ antioxidant in combination with a glycolysis inhibitor. Inhibition of glycolysis increases mROS production due to increased activity of mitochondria. One way to inhibit glycolysis is to inhibit 6-phosphofructo-2-kinase (PFK-2) using any known PFK-2 inhibitor. For example, PFK-2 can be inhibited with 3-(3-pyridinyl)-1-(4-pyridinyl)-2-proper-1-one (3PO) (Clem, et al., Mol. Cancer Ther 7:110-20 (2008)). A combination of mitochondrially-targeted antioxidants, including SkQs, and glycolysis inhibitors is a powerful treatment for AD and other neurodegenerative diseases.

Equivalents

Those skilled in the art will recognize, or be able to ascertain, using no more than routine experimentation, numerous equivalents to the specific embodiments described specifically herein. Such equivalents are intended to be encompassed in the scope of the claims appended hereto.

The invention claimed is:

1. A method for providing to a mammal a neuroprotective effect against a brain pathology that is mediated by reactive oxygen species originating from mitochondria (mROS), wherein the brain pathology is selected from the group consisting of alcohol intoxication, hyperhomocysteinemia, and brain trauma, the method comprising the step of administering to the mammal an SkQ mitochondria-targeted antioxidant in an amount effective to provide said neuroprotective effect, wherein the SkQ mitochondria-targeted antioxidant is administered either prophylactically to inhibit the course of the pathology or for treatment of the pathology after its onset with the exception that, where the pathology is brain trauma, the SkQ mitochondria-targeted antioxidant is administered only for treatment after onset of the pathology.

2. The method according to claim 1, wherein the SkQ mitochondria-targeted antioxidant is selected from the group consisting of SkQ1 and SkQR1.

3. The method according to claim 1, wherein the SkQ mitochondria-targeted antioxidant is administered to the mammal in an amount of about 1pmole to 1 mmole per kg of body weight of the mammal per day.

4. The method according to claim 1, wherein the brain pathology comprises alcohol intoxication.

5. The method according to claim 4, wherein the SkQ mitochondria-targeted antioxidant is administered to the mammal after the mammal has undergone alcohol narcosis.

6. The method according to claim 1, wherein the brain pathology is hyperhomocysteinemia.

7. The method according to claim 6, wherein the mammal is a pregnant human.

8. The method according to claim 1, wherein the SkQ mitochondria-targeted antioxidant is administered to the mammal prior to an appearance in the subject of behavioral defects due to the brain pathology.

9. The method according to claim 1, wherein the SkQ mitochondria-targeted antioxidant is administered to the mammal after the mammal has contracted the brain pathology or after an appearance in the subject of behavioral defects due to the brain pathology.

10. The method according to claim 1, wherein the brain pathology is brain trauma.

11. The method according to claim 10, wherein the SkQ mitochondria-targeted antioxidant is administered to the mammal daily after the mammal has experienced the brain trauma for a period of at least 4 days after the trauma.

12. The method according to claim 1, wherein the SkQ mitochondria-targeted antioxidant is administered to the mammal by a mode of administration selected from the group consisting of intradermal, intramuscular, intraperitoneal, intravenous, subcutaneous, intranasal, epidural, oral, sublingual, intracerebral, intravaginal, transdermal, rectal, by inhalation and topical.

13. The method according to claim 1, wherein the SkQ mitochondria-targeted antioxidant is administered to the mammal in combination with a glycolysis inhibitor.

14. A method for providing to a mammal a neuroprotective effect against a brain pathology, wherein the brain pathology is brain trauma, the method comprising the step of administering to the mammal an SkQ mitochondria-targeted antioxidant in an amount effective to initiate an increased production of erythropoietin in the mammal.

15. A method for providing to a mammal a neuroprotective effect against a brain pathology, wherein the brain pathology is brain trauma, the method comprising the step of administering to the mammal an SkQ mitochondria-targeted antioxidant in an amount effective to cause a decrease in activity of glycogen synthase kinase (GSK-3β) in the mammal.

* * * * *